United States Patent
Arens et al.

(10) Patent No.: US 11,291,754 B2
(45) Date of Patent: Apr. 5, 2022

(54) SYSTEM FOR THE EXTRACORPOREAL ELIMINATION OF CARBON MONOXIDE

(71) Applicant: Rheinisch-Westfaelische Technische Hochschule Aachen, Aachen (DE)

(72) Inventors: Jutta Arens, Aachen (DE); Ralf Borchardt, Aachen (DE); Peter Christian Schlanstein, Aachen (DE); Thomas Schmitz-Rode, Aachen (DE); Lotte Schraven, Aachen (DE); Georg Wagner, Aachen (DE); Ulrich Steinseifer, Hauset (BE)

(73) Assignee: RHEINISCH-WESTFAELISCHE TECHNISCHE HOCHSCHULE (RWTH) AACHEN, Aachen (DE)

( * ) Notice: Subject to any disclaimer, the term of this patent is extended or adjusted under 35 U.S.C. 154(b) by 761 days.

(21) Appl. No.: 16/084,129

(22) PCT Filed: Feb. 14, 2017

(86) PCT No.: PCT/EP2017/000202
§ 371 (c)(1),
(2) Date: Sep. 11, 2018

(87) PCT Pub. No.: WO2017/153034
PCT Pub. Date: Sep. 14, 2017

(65) Prior Publication Data
US 2020/0289736 A1 Sep. 17, 2020

(30) Foreign Application Priority Data

Mar. 11, 2016 (DE) .......................... 102016002950.1

(51) Int. Cl.
*A61M 1/16* (2006.01)
*A61M 1/36* (2006.01)
(Continued)

(52) U.S. Cl.
CPC ............ *A61M 1/32* (2013.01); *A61M 1/1645* (2014.02); *A61M 1/1698* (2013.01); *A61M 1/30* (2013.01);
(Continued)

(58) Field of Classification Search
CPC ............ A61M 1/1645; A61M 1/16983; A61M 1/304; A61M 1/32; A61M 1/322;
(Continued)

(56) References Cited

U.S. PATENT DOCUMENTS 3,807,958 A * 4/1974 Brumfield ............. A61M 1/322
422/46
4,048,705 A 9/1977 Blanpain et al.
(Continued)

FOREIGN PATENT DOCUMENTS

DE 32 32 716 A1 3/1984
DE 19905937 C1 7/2000
(Continued)

OTHER PUBLICATIONS

Yin L., et al. "Treatment of acute carbon monoxide poisoning with extracorporeal membrane trioxygenation", Int J Artif Organs 2012: 35(12): 1070-1076.
(Continued)

*Primary Examiner* — Benjamin J Klein
(74) *Attorney, Agent, or Firm* — Norris McLaughlin, P.A.

(57) ABSTRACT

A system for the extracorporeal elimination of carbon monoxide, includes at least one pump and a gas exchange chamber, wherein the at least one pump can be connected to the blood circulatory system of a person by way of a first tube section connectable to a cannula and is connected to a gas exchange chamber via a second tube section, wherein the system is configured to transfer blood, via the first tube section, from the blood circulatory system of the person by (Continued)

way of at least one pump into the gas exchange chamber, and to return the blood from the gas exchange chamber to the blood circulatory system of the person via the same first tube section.

25 Claims, 2 Drawing Sheets (51) Int. Cl.
*A61M 1/32* (2006.01)
*A61M 1/30* (2006.01)

(52) U.S. Cl.
CPC ............ *A61M 1/304* (2014.02); *A61M 1/322* (2014.02); *A61M 1/3659* (2014.02); *A61M 2202/0233* (2013.01); *A61M 2205/3331* (2013.01); *A61M 2205/3337* (2013.01); *A61M 2205/75* (2013.01)

(58) Field of Classification Search
CPC ........ A61M 1/3659; A61M 2202/0233; A61M 2205/3331; A61M 2205/3337; A61M 2205/75; A61M 2207/08
See application file for complete search history.

(56) References Cited

U.S. PATENT DOCUMENTS

| | | | |
|---|---|---|---|
| 4,203,188 A | 5/1980 | Blanpain et al. | |
| 4,336,224 A | 6/1982 | Siposs | |
| 4,828,543 A * | 5/1989 | Weiss | A61M 1/303 604/6.09 |
| 5,643,215 A * | 7/1997 | Fuhrman | A61M 1/3621 604/151 |
| 9,833,823 B2 | 12/2017 | Sprock | |
| 2007/0166189 A1 * | 7/2007 | Ogihara | A61M 1/3627 422/45 |
| 2010/0047616 A1 | 2/2010 | Urevich | |
| 2012/0172781 A1 | 7/2012 | Wang | |
| 2012/0226258 A1 | 9/2012 | Otto et al. | |
| 2013/0230602 A1 * | 9/2013 | Grady | A61M 5/14 424/613 |
| 2016/0296685 A1 * | 10/2016 | Wu | A61M 1/1629 |

FOREIGN PATENT DOCUMENTS

| | | | | |
|---|---|---|---|---|
| DE | 19916234 A1 | 9/2000 | | |
| EP | 0 240 101 A2 | 10/1987 | | |
| FR | 2974528 A1 | 11/2012 | | |
| RU | 2635500 C2 | 11/2017 | | |
| UA | 864 A1 | 12/1993 | | |
| WO | 00/64522 A1 | 11/2000 | | |
| WO | 2005/028002 A1 | 3/2005 | | |
| WO | WO-2005028002 A1 * | 3/2005 | ............. | A61M 1/30 |
| WO | 2012/082257 A1 | 6/2012 | | |

OTHER PUBLICATIONS

Wang G.S., et al. "Extracorporeal Membrane Oxygenation (ECMO) for Severe Toxicological Exposures: Review of the Toxicology Investigators Consortium (ToxIC)", J. Med. Toxicol. (2016) 12:95-99.

Teerapuncharoen K., et al. "Successful Treatment of Severe Carbon Monoxide Poisoning and Refractory Shock Using Extracorporeal Membrane Oxygenation", Respiratory Care, epub ahead of print on Apr. 28, 2015 as DOI: 10.4187/respcare.03990.

McCunn M., et al. "Extracorporeal support in an adult with severe carbon monoxide poisoning and shock following smoke inhalation: a case report", Perfusion 2000: 15: 169-173.

* cited by examiner

SYSTEM FOR THE EXTRACORPOREAL ELIMINATION OF CARBON MONOXIDE

BACKGROUND OF THE INVENTION

The invention relates to a system for the extracorporeal elimination of carbon monoxide, comprising at least one pump and a gas exchange chamber, wherein at least one pump can be connected to the blood circulatory system of a person by way of a first tube section connectable to a cannula, and is connected to a gas exchange chamber via a second tube section.

Hemoglobin in the blood is available for binding oxygen ($O_2$), oxygen being bound to the iron atoms in the hemoglobin, whereby oxygen is transported by the blood stream from the lungs to other organs and tissues. Similarly to the manner in which oxygen binds to hemoglobin, carbon monoxide (CO) also binds to hemoglobin, the affinity being up to 300 times greater than that of oxygen. When an iron atom is "blocked" by a carbon monoxide molecule, the atom is no longer available for binding an oxygen molecule. The blocking caused by carbon monoxide binding to the hemoglobin lowers the ability of the blood to take up and transport oxygen, putting the patient at risk of internal suffocation. Additionally, carbon monoxide finds its way into the body's circulatory system together with the blood and deposits in organs, for example in the cardiac muscle tissue, where it can bind to myoglobin, causing insufficient supply of oxygen to the heart, resulting in cardiac infarction.

In the case of mild carbon monoxide poisoning, treatment by way of medication, and/or oxygen therapy, may be initiated. Severe cases of carbon monoxide poisoning, however, require the patient to receive hyperbaric oxygen (HBO) therapy in a pressure chamber to be effective. Within the scope of HBO therapy, the patient is placed into a pressure chamber and breathes in oxygen via a mask, and the ambient pressure in the chamber is raised. The increased partial pressure of oxygen or the physically dissolved oxygen fraction in the blood, resulting from the inhalation of pure oxygen and the increased ambient pressure, eliminates carbon monoxide significantly more rapidly from the blood.

The elimination of carbon monoxide by way of HBO therapy is a relatively slow process, which must be carried out over a duration of minutes to hours. Additionally, there are a limited number of HBO centers. In Germany, for example, there are 25 HBO centers, which are disproportionately distributed throughout the nation, so that fast and nationwide HBO therapy in the case of carbon monoxide poisoning is not ensured. It is important, however, to treat carbon monoxide poisoning quickly, so as to restore the patients oxygen supply and minimize spreading of the carbon monoxide. This allows subsequent severe damage or a fatal outcome due to oxygen deficiency to be prevented.

A method and a system for treating carbon monoxide poisoning are described in patent document WO 2012/082257 A1. Hemoglobin loaded with carbon monoxide (COHb) is pumped from the blood circulatory system of a person into a filtration unit by way of a pump. In the filtration unit, the carbon monoxide is exchanged with oxygen and supplied, via a second tube, to the blood circulatory system of the patient. The filtration unit is designed so that the blood and an extraction medium, which is separated by a gas permeable membrane, flow tangentially past one another. A gas exchange takes place through the gas permeable membrane between the extraction medium, which is enriched with oxygen, and the hemoglobin loaded with carbon monoxide. In this way, no direct contact is possible between the blood and the extraction medium, which represents an additional hurdle for effective gas exchange. Flow through the filtration unit takes place unidirectionally, whereby only a continuous process can be carried out with the described system in which, during the treatment, the blood loaded with carbon monoxide is first pumped out of the body via a first cannula, and blood enriched with oxygen is returned to the circulatory system by way of a second cannula. This method therefore necessitates inserting two cannulas in the patient. In addition, a second circuit system comprising an additional pump for the extraction medium is required, which increases the complexity of this design.

SUMMARY OF THE INVENTION

It is the object of the present invention to provide a simple system for the extracorporeal elimination of carbon monoxide, which has a low need for maintenance, allows for mobile use, can be connected to the blood circulatory system of a person in a minimally invasive manner, and can be operated with the simplest of means.

According to the invention, this object is achieved by a system for the extracorporeal elimination of carbon monoxide which is configured to transfer blood, via a first tube section, from the blood circulatory system of a person by way of at least one pump, in particular via a second tube section, into a gas exchange chamber, and to return the blood from the gas exchange chamber to the blood circulatory system of a person via the same first tube section.

By removing the blood via the first tube section in this system, and also returning the blood to the body via the same first tube section, it is possible to achieve an extracorporeal elimination of carbon monoxide by establishing a single access. Via the first tube section, the system thus allows hemoglobin loaded with carbon monoxide to be treated in portions in the gas exchange chamber. The first tube section and the second tube section can preferably be formed by the same continuous tube.

Advantageously, a minimally invasive approach for the extracorporeal elimination of carbon monoxide is thus achieved, since only a single access to the blood circulatory system of the person is needed, instead of two accesses. Moreover, the time that is needed to get the system ready for use is significantly reduced, since the establishment of a second access is eliminated. In addition, the fill volume of the system is lower since it is not necessary to fill a second access comprising a tube system with blood for operation.

According to an advantageous embodiment of the invention, the system comprises a pump that can be operated bidirectionally.

In this way, it is possible to transfer the blood via only a single tube and by way of only one pump from the blood circulatory system of a person into the gas exchange chamber, and to return this from the gas exchange chamber to the blood circulatory system. When the pump, which can be operated bidirectionally, is operated in a first pumping direction or rotational direction, the blood is thus transferred from the blood circulatory system of a person into a gas exchange chamber. In the case of the opposite rotational direction, the blood enriched with oxygen is returned to the blood circulatory system of the person.

The use of a bidirectional pump has the advantage that only one pump is needed to treat the blood in portions in the gas exchange chamber, which results in as simple a design as possible, which is easy to control and inexpensive to implement. Moreover, the use of only one bidirectional pump saves space and weight so that, advantageously, a system for the extracorporeal elimination of carbon monoxide can be implemented which can be transported.

A further embodiment of the invention provides for the first tube section, which can be connected via a cannula to the blood circulatory system of the person, to be connected to two unidirectionally operable pumps. The first tube section is preferably divided by way of a Y connector and connected thereby to the two unidirectionally operable pumps.

As a result of the use of two unidirectionally operable pumps, it is possible to treat the blood in portions in the gas exchange chamber. For this purpose, for example, a first pump is activated so as to transfer the blood from the blood circulatory system of the person into the gas exchange chamber. A second unidirectional pump is activated so as to return the blood from the gas exchange chamber to the blood circulatory system of the person. Based on the first tube section, the two pumps thus pump in opposite directions.

The use of two unidirectional pumps has the advantage that it is possible to use comparatively inexpensive pumps for creating the system according to the invention, which additionally are highly reliable.

According to a particularly preferred further embodiment of the invention, the pump is, or the pumps are, peristaltic pumps.

The medium to be pumped is forced through a tube as a result of outside mechanical deformation thereof. Due to the use of a peristaltic pump, the blood can thus be removed via a tube from the blood circulatory system of the person, and returned thereto, without making contact with other components of the pump.

This offers the advantage that the pump itself does not have to be cleaned when switching to new patients, but rather only the tube has to be replaced so as to prevent blood from different patients being exchanged. Due to the use of peristaltic pumps, hygienic cleaning of the system for the extracorporeal elimination of carbon monoxide is thus possible.

Another embodiment variant of the invention provides for flow between the first tube section and the second tube section to be prevented by the pump, or the pumps, when these are deactivated and not pumping.

The first tube section can be connected to a cannula, while the second tube section is connected to the gas exchange chamber.

For example, it is possible to prevent the flow in the deactivated state when using a peristaltic pump since the mechanical deformation of the tube from the outside has the effect that fluid cannot pass through this tube. By using a pump that, when deactivated, prevents a flow between the first tube section or the blood circulatory system of a person and the second tube section or the gas exchange chamber, it is possible to achieve a separation between the blood circulatory system of a person and the gas exchange chamber in a simple manner. In particular, the gas exchange chamber can be operated when the pumps are deactivated, without influencing the blood circulatory system of the person.

The use of pumps which, when deactivated, prevent a flow, offers the advantage of achieving effective separation between the blood circulatory system and the gas exchange chamber, without the need for additional valves. This enables a space-saving, simple and low-maintenance implementation of a system for the extracorporeal elimination of carbon monoxide.

In a further embodiment of the invention, it is provided that a bubble filter is disposed between the second tube section and the gas exchange chamber.

The use of a bubble filter causes gas bubbles present in the treated blood to be filtered out. In particular, a bubble filter causes blood from the gas exchange chamber, which may include gas bubbles after elimination of carbon monoxide and enrichment with oxygen, to be freed of these gas bubbles prior to being returned to the blood circulatory system of the person.

This has the advantage that bubble-free blood is returned from the gas exchange chamber to the blood circulatory system of the person, and negative effects due to excessively large gas bubbles in the blood circulatory system are thereby prevented.

An advantageous embodiment of the invention provides for the bubble filter between the second tube section and the gas exchange chamber to include pores having a diameter in the range of 5 to 80 µm. Pores of this size prevent gas bubbles having a larger diameter from flowing through. For example, a corresponding bubble filter may be formed by a membrane or a foam or a textile. Particularly preferably, a woven plastic fabric is used as the bubble filter. Moreover, it is provided to attach the bubble filter to the gas exchange chamber by way of a screw joint and/or a locking device. Another embodiment may provide that the bubble filter is integrated into the gas exchange chamber.

Such a design of the bubble filter advantageously causes the blood being returned to the blood circulatory system of the person to include only oxygen bubbles that do not adversely affect the blood circulatory system. By virtue of fastening by way of a screw joint and/or locking device, it is advantageously possible to easily replace the bubble filter as needed.

In a particularly preferred embodiment, it is provided that the gas exchange chamber comprises an oxygen supply system, which is connected to an oxygen source via an oxygen supply line. The oxygen source preferably includes an oxygen-containing gas mixture having a high oxygen concentration, and in particular an oxygen concentration of more than 95%.

In this way, oxygen is added to the gas exchange chamber, in which the hemoglobin loaded with carbon monoxide is present. Mixing the hemoglobin loaded with carbon monoxide with oxygen causes the carbon monoxide to be replaced with oxygen and, as a result, carbon monoxide to be eliminated from the blood. Contact between oxygen and hemoglobin loaded with carbon monoxide has the advantage that a direct exchange takes place, and other components, such as membranes, may be dispensed with.

By virtue of the supply of oxygen and the direct contact between oxygen and blood, the gas exchange chamber according to the invention is easy to implement and, compared to other technologies, is low-maintenance.

A particularly effective variant embodiment of the invention provides for pressure above the ambient atmospheric pressure, such as 0.5 to 10 bar above, to be applicable to the gas exchange chamber.

The application of pressure to the gas exchange chamber causes the contact between the hemoglobin loaded with carbon monoxide and the oxygen to take place at a pressure that positively influences the exchange of carbon monoxide with oxygen.

Advantageously, applying pressure to the gas exchange chamber results in a more effective and faster elimination of the carbon monoxide in the blood, and thus in faster treatment of the patient.

In a particularly practical design of the invention, the oxygen source is an oxygen cylinder. In this particularly practical design, the oxygen cylinder is filled with pure oxygen or a gas mixture having a very high oxygen content. The use of an oxygen cylinder provides the option of supplying oxygen to the gas exchange chamber via the oxygen supply line and the oxygen supply system, and thereby achieving the exchange with the carbon monoxide. A gas cylinder has the advantage that this is able to build pressure, and moreover is typically available in rescue vehicles or treatment rooms. Moreover, oxygen cylinders are produced in very large quantities, allowing an inexpensive solution for a system for the extracorporeal elimination of carbon monoxide to be implemented. Oxygen cylinders are furthermore also available in small sizes, which makes the system mobile and transportable.

Another embodiment of the invention is characterized in that the oxygen supply system comprises an effusion element, which is configured to form gas bubbles.

As a result of the use of an effusion element configured to form gas bubbles, a large number of gas bubbles are formed in the blood, which are present in the gas exchange chamber, whereby the effective interaction surface between oxygen and blood is increased.

Increasing the effective interaction surface between blood and oxygen causes exchange of the carbon monoxide with oxygen to take place more quickly, whereby efficient elimination of carbon monoxide from the blood can be achieved.

In a particularly practicable design of the invention, it is provided that the effusion element is a perforated line, a perforated membrane or a porous foam.

As a result of the use of a perforated line, a perforated membrane or a porous foam, it is possible to effectively produce gas bubbles in the gas exchange chamber and, in this way, ensure effective exchange of carbon monoxide with oxygen to as great an extent as possible. Using a perforated line, a perforated membrane or a porous foam as the effusion element has the advantage that the desired gas bubbles can be easily produced in the blood in the gas exchange chamber using conventional components.

Another embodiment of the invention provides for the gas exchange chamber to comprise a carbon monoxide discharge line.

The carbon monoxide, which has been replaced in the blood with oxygen and is therefore present in a gaseous state in the gas exchange chamber, is discharged therefrom via the carbon monoxide discharge line. The carbon monoxide discharge line is furthermore used to remove oxygen that was not taken up by the hemoglobin of the blood in the gas exchange chamber. In this way, the gaseous waste products of the elimination of carbon monoxide are removed from the gas chamber.

Advantageously, the concentration of carbon monoxide in the gas exchange chamber is kept low compared to the oxygen concentration, whereby effective exchange between carbon monoxide and oxygen is achieved.

In a further preferred variant embodiment of the invention, it is provided that a foam filter is disposed between the gas exchange chamber and the carbon monoxide discharge line. Advantageously, it may also be provided that the foam filter is integrated into the gas exchange chamber. Another embodiment may provide that the foam filter is replaceably disposed on the gas exchange chamber.

The foam filter is used to suppress the exit of foamed blood, which forms in the gas exchange chamber when supplying the oxygen bubbles.

Advantageously, blood is prevented from exiting, whereby a loss of blood through the system for the extracorporeal elimination of carbon monoxide is prevented.

A further embodiment of the invention provides for the oxygen supply line to comprise a first valve, and for the carbon monoxide discharge line to comprise a second valve, which can, in particular, each be activated.

Using these two valves makes it possible, to supply oxygen to the gas exchange chamber, and/or to remove carbon monoxide and oxygen from the gas exchange chamber, as needed. In this way, the pressure inside the gas exchange chamber and the flow of oxygen, in the form of gas bubbles, through the blood, can be controlled, so that effective elimination of carbon monoxide can be established.

Advantageously, the first and second valves make it possible to optimally set the pressure, and the oxygen through-flow and oxygen concentration in the gas exchange chamber, and to treat the blood in portions therein, for effective and fast elimination of carbon monoxide from the hemoglobin and oxygen enrichment of the hemoglobin.

According to a further variant embodiment of the invention, the first tube section or the second tube section comprises at least one third valve. Preferably, the third valve is disposed between the bubble filter and the pump.

Flow between the blood circulatory system and the gas exchange chamber can be prevented by a third valve, which is located between the blood circulatory system of the person and the gas exchange chamber. In particular, a third valve makes it possible to close the gas exchange chamber in a pressure-tight manner, so that optimal pressure for the elimination of carbon monoxide can be applied thereto.

The use of a third valve offers the advantage that the blood circulatory system of the person can be easily separated from the gas exchange chamber. In particular, a third valve makes it possible to design the system according to the invention with pumps that, when deactivated, do not prevent a flow. Disposing the third valve between the bubble filter and the pump offers the advantage that pressure variation due to the operation of the valve in the first tube section, such as would affect the blood circulatory system of the person, is reduced or prevented.

In a further variant embodiment of the invention, it is provided that the gas exchange chamber comprises a first sensor unit that can be used to determine a carbon monoxide concentration. For example, the carbon monoxide concentration in the blood and/or in the gas can be measured.

The use of a carbon monoxide sensor provides the option of deliberately controlling the valves of the oxygen supply line, and/or of the carbon monoxide discharge line, in particular as a function of the measured concentration of carbon monoxide, and thus achieving a desired carbon monoxide concentration in the gas exchange chamber. In particular, it is possible to establish, as a function of the carbon monoxide concentration, when the elimination of carbon monoxide from the blood has progressed sufficiently to return the blood enriched with oxygen to the blood circulatory system of the person, and thus when it is possible to advantageously treat the blood in portions as needed.

A carbon monoxide sensor thus has the advantage that the process for eliminating carbon monoxide can be established and optimized based on the determined carbon monoxide concentration.

In a further preferred variant embodiment of the invention, it is provided that the gas exchange chamber comprises a second sensor unit, which can be used to measure a pressure inside the gas exchange chamber.

By way of the pressure inside the gas exchange chamber, as determined by the pressure sensor, it is possible to set the supply of oxygen via the oxygen supply line, and the removal of carbon monoxide via the carbon monoxide discharge line, so that a desired pressure can be achieved and maintained for a period, or a pressure curve can be followed, and in particular so that optimal elimination of carbon monoxide takes place.

In a further variant embodiment of the invention, the system comprises a flow meter, which determines the amount of blood that is transferred into, and/or out of, the gas exchange chamber. Moreover, it may be provided in one embodiment to dispose an oxygen flow sensor, and/or an oxygen concentration sensor, on the oxygen supply line, and/or a carbon monoxide flow sensor, and/or a carbon monoxide concentration sensor, on the carbon monoxide discharge line. Advantageously, a level sensor is integrated into the gas exchange chamber, which determines the blood level inside the gas exchange chamber.

Using these additional sensors allows the system according to the invention to be optimally controlled, and efficient elimination of carbon monoxide to as great an extent as possible to be achieved. For example, the supply of oxygen and the discharge of carbon monoxide may be set to an identical value so that continuous generation of gas bubbles is achieved at a constant pressure, which, in particular, is above the atmospheric pressure.

In a particularly preferred variant embodiment of the invention, the system is configured to treat the blood in portions, wherein, in a first operating mode, blood is pumped from the blood circulatory system of the person into the gas exchange chamber. For this purpose, in the first operating mode, for example, the first valve is closed completely or partially, the second valve is opened completely or partially, and the pump is activated in such a way that the blood is pumped into the gas exchange chamber. Due to the second valve being opened, the blood being pumped by the pump in the direction of the gas exchange chamber is able to flow into the chamber, without a counter pressure building therein. It may, in particular, be advantageous if no or little oxygen is introduced when the blood is being pumped into the gas exchange chamber, so as to avoid wasting oxygen unnecessarily.

Another embodiment of the invention provides for the system to be configured to treat blood in portions, wherein, in a second operating mode, blood in the gas exchange chamber is brought in contact with oxygen under increased pressure. In the second operating mode, for example, the pump is deactivated, and the degrees of opening of the first valve and of the second valve are varied, wherein, in a particularly practical design, the degree of opening of the first valve, and/or of the second valve, is not controlled suddenly, but in a time-controlled manner. So as to build pressure inside the gas exchange chamber, for example, the first valve is opened completely or partially, and the second valve is closed completely or partially. So as to continuously supply oxygen at a constant pressure, the degrees of opening of the first valve and of the second valve are set so that the oxygen supply and the carbon monoxide discharge take on an identical value. So as to reduce pressure inside the gas exchange chamber, for example, the first valve is closed completely or partially, and the second valve is opened completely or partially.

Since the pump is deactivated and the second valve is completely or partially closed, no liquid can escape from the gas exchange chamber. As a result of the first valve being opened completely or partially, oxygen is introduced into the gas exchange chamber, and an increased pressure is formed in the gas exchange chamber. Moreover, by deliberately setting an oxygen supply by way of the first valve, and deliberately setting a carbon monoxide discharge by way of the second valve, a continuous through-flow of oxygen can be achieved at a certain pressure, so that a constant formation of oxygen bubbles over time can be achieved. Reducing the pressure inside the gas exchange chamber by way of the second valve makes it possible to adapt the pressure in the gas exchange chamber to the atmospheric pressure again, so that the pressure inside the gas exchange chamber is adjusted to the pressure of the blood circulatory system. The second operating mode, in this way, offers the advantage that effective elimination of carbon monoxide can be effectively carried out in the gas exchange chamber at increased pressure, using a high oxygen/blood contact surface.

In a preferred embodiment, the second valve is a pressure control valve, which automatically reduces pressure when the desired pressure is exceeded by the supply of oxygen, so that the pressure remains constant when oxygen is being supplied.

In another embodiment of the invention, it is provided that the system is configured to treat blood in portions, wherein, in a third operating mode, blood is pumped from the gas exchange chamber back into the blood circulatory system of the person. In this operating mode, for example, the first valve is closed completely or partially, the second valve is opened completely or partially, and the pump is activated in such a way that the blood is pumped from the gas exchange chamber into the blood circulatory system of the person. In a particularly practical design, the closing of the first valve, and/or the opening of the second valve, can take place not suddenly, but in a time-controlled manner.

When the blood is returned to the blood circulatory system, the first valve, which is to say the oxygen supply system, is closed so as to avoid the unnecessary consumption of oxygen. The second valve in the carbon monoxide discharge line is open, for example, in the third operating mode so as to achieve a simpler return of the blood to the blood circulatory system.

The treatment of blood in portions by consecutively carrying out the first, second and third operating modes advantageously enables effective elimination of carbon monoxide, wherein only one access to the blood circulatory system of the person has to be established. In this way, the system according to the invention can be placed in service on the person quickly and in a minimally invasive manner. Repeatedly carrying out the treatment of blood in portions by consecutively carrying out the first, second and third operating modes advantageously makes it possible to effectively eliminate carbon monoxide from the blood circulatory system of the person in increments.

A particularly practicable variant embodiment of the invention provides for the system to comprise a control unit, which is configured to control the pump, and/or the first valve, and/or the second valve, and/or to read out the first sensor unit, and/or the second sensor unit.

Using a control unit that controls, and/or reads out, the components of the system, as needed, enables efficient control of the system according to the invention. The control unit is, in particular, designed to consecutively carry out the first operating mode, the second operating mode, and the third operating mode. Moreover, by evaluating the pressure and the carbon monoxide concentration by way of the first and second sensor units, the operating modes can be optimized to the effect that the elimination of carbon monoxide can be carried out as effectively as possible.

A particularly user-friendly embodiment of the invention provides for the system to be transportable in a mobile manner in a portable case, both when not in use and when in use on a person.

Due to the fact that the system can be accommodated in a case and can be transported, it is ensured that the system according to the invention for the elimination of carbon monoxide can be transported in a mobile manner in ambulances, or rescue vehicles or emergency physician vehicles. In this way, it is advantageously ensured that elimination of carbon monoxide can also be carried out directly and locally outside a hospital, at the site of an accident, so that fast treatment of the patient is ensured, and consequently subsequent damage from carbon monoxide poisoning is reduced.

BRIEF DESCRIPTION OF THE DRAWINGS

Embodiments of the invention will be introduced and described in more detail hereafter based on figures. In the drawings.

DETAILED DESCRIPTION OF THE INVENTION

Figure 1:
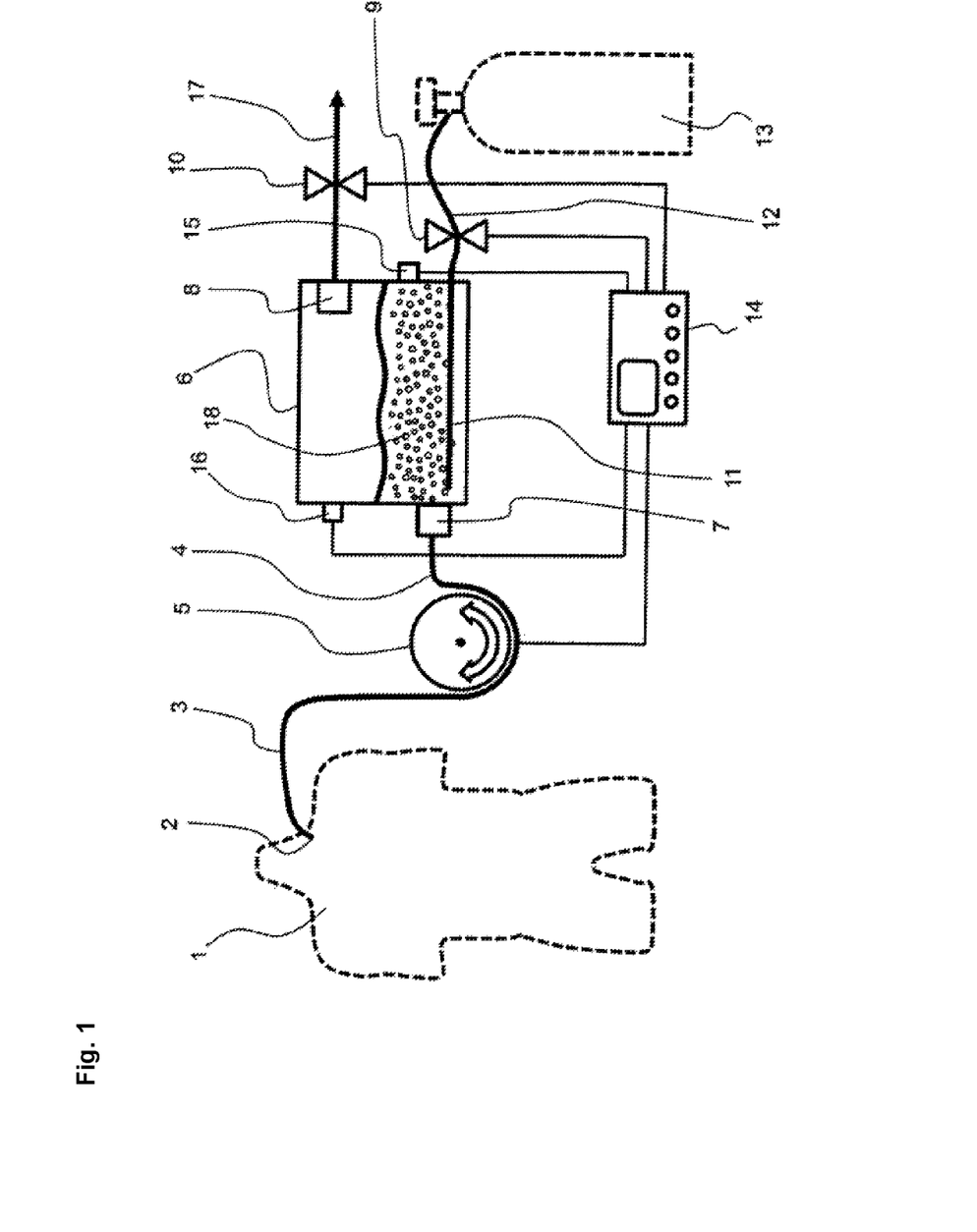
FIG. 1 shows the schematic composition of the system according to the invention comprising one bidirectional pump.

FIG. 1 shows the system according to the invention for the extracorporeal elimination of carbon monoxide in a schematic illustration, wherein the person 1 can be connected via a cannula 2 and via a tube, comprising a first tube section 3 and a second tube section 4, to the gas exchange chamber 6. The pump 5 used in this exemplary embodiment is a bidirectional pump 5, which either pumps blood from the blood circulatory system of the person 1 into the gas exchange chamber 6, or pumps blood from the gas exchange chamber 6 back into the blood circulatory system of the person 1, or suppresses a flow. In this way, it is possible to implement a system for the extracorporeal elimination of carbon monoxide, by way of a single connecting site to the blood circulatory system of the person 1 formed by the cannula 2.

In a preferred embodiment, the pump 5 is a peristaltic pump, which can be operated bidirectionally. A peristaltic pump offers the option of being operated bidirectionally in a simple manner, and of preventing a flow between the first tube section 3 and the second tube section 4 when deactivated. Moreover, only the first tube section 3 and the second tube section 4 come in contact with the blood, so that cleaning of the pump is eliminated, which has advantages, in particular for hygienic reasons.

In the variant embodiment shown in FIG. 1, a bubble filter 7 is disposed between the second tube section 4 and the gas exchange chamber 6, which prevents gas bubbles 18 formed in the gas exchange chamber 6 from being returned to the blood circulatory system of the person 1. Advantageously, the bubble filter 7 includes pores having a diameter in the range of 5 to 80 μm, so that gas bubbles 18 that may be returned to the blood circulatory system of the person 1 have no adverse effects there. The bubble filter 7 is preferably a membrane or a foam or a textile. It is particularly preferred when the bubble filter is a woven plastic fabric.

The embodiment of the invention shown in FIG. 1 comprises an oxygen supply system 11, which is connected to an oxygen source 13 via an oxygen supply line 12. By virtue of the oxygen supply system, oxygen is introduced into the gas exchange chamber 6, and a high oxygen concentration is thus created inside the gas exchange chamber 6. This causes the hemoglobin loaded with carbon monoxide to come in contact with oxygen, and the carbon monoxide to be exchanged with oxygen. In this way, carbon monoxide is eliminated from the blood in the gas exchange chamber 6. Advantageously, a pressure in the range of 0.5 bar to 10 bar above the ambient atmospheric pressure is applied to the gas exchange chamber 6, so that the elimination takes place at an elevated pressure, and thus progresses more effectively. The oxygen source 13 used is preferably an oxygen cylinder, which not only applies the necessary pressure, but is also usually available in ambulances as well as in treatment rooms.

In an embodiment of the invention which is not shown, the oxygen supply system 11 comprises an effusion element, which is configured to form gas bubbles 18. The effusion element can be formed by a perforated line, a perforated membrane or by a porous foam.

As is shown in FIG. 1, in one variant embodiment, the gas exchange chamber 6 comprises a carbon monoxide discharge line 17, via which carbon monoxide and/or oxygen can escape from the gas exchange chamber 6. Furthermore, a foam filter 8, which ensures that only gases, which is to say oxygen and/or carbon monoxide, actually escape from the gas exchange chamber 6, is disposed between the gas exchange chamber 6 and the carbon monoxide discharge line 17. The blood, provided with gas bubbles 18, which is present in the gas exchange chamber 6, is thus not transferred out of the gas exchange chamber 6.

In the illustrated variant embodiment, the oxygen supply line 12 comprises a first valve 9. The first valve 9 can be used to control the supplied amount of oxygen in the gas exchange chamber 6. Furthermore, the carbon monoxide discharge line 17 comprises a second valve 10, which can be used to control the pressure inside the gas exchange chamber 6, and/or the removal of carbon monoxide, and/or oxygen. In this way, it is ensured that the process-related waste products are removed from the gas exchange chamber 6, and the pressure inside the gas exchange chamber 6 can be regulated.

In a variant embodiment which is not shown, the first tube section 3 or the second tube section 4 comprises at least one third valve. By way of a third valve, flow can be prevented between the blood circulatory system of the person 1 and the gas exchange chamber 6, and thus it is also possible to use pumps for the system according to the invention which allow a flow when not pumping. Moreover, the use of a third valve allows a higher pressure to be applied to the gas exchange chamber 6. The third valve is preferably disposed between the pump 5 and the bubble filter 7.

As is shown in FIG. 1, a first sensor unit 15 is disposed on the gas exchange chamber 6, by way of which a carbon monoxide concentration can be determined, wherein the measurement of the carbon monoxide concentration allows optimal control of the system to be implemented. In particular, the first sensor unit 15 ensures that only blood having a sufficient oxygen concentration, and/or a sufficiently low carbon monoxide concentration, is returned to the blood circulatory system of the person 1. In the illustrated embodiment, the gas exchange chamber 6 comprises a second sensor unit 16, which can be used to measure a pressure inside the gas exchange chamber 6. This pressure sensor makes it possible to optimally set the pressure inside the chamber. In particular, the degree of opening of the first valve 9, and/or of the second valve 10, can be variably set so as to ensure optimal pressure, and/or an optimal pressure curve, in the gas exchange chamber 6.

In a further embodiment of the invention, which is not shown, the system for the elimination of carbon monoxide comprises a flow meter, which determines the amount of blood that is transferred into and/or out of the gas exchange chamber. Moreover, it may be provided, in one embodiment, that an oxygen flow sensor, and/or an oxygen concentration sensor, is disposed on the oxygen supply line, and/or a carbon monoxide flow sensor, and/or a carbon monoxide concentration sensor, is disposed on the carbon monoxide discharge line. Advantageously, a level sensor is further integrated into the gas exchange chamber, which determines the blood level inside the gas exchange chamber. Using these additional sensors makes it possible to optimally control the system according to the invention, and to achieve efficient elimination of carbon monoxide to as great an extent as possible. The supply of oxygen and the discharge of carbon monoxide, for example, can be set to an identical value so that continuous generation of bubbles is achieved at a constant pressure, which, in particular, is above the atmospheric pressure.

As is shown in FIG. 1, a variant embodiment of the invention comprises a control unit 14, which is configured to control the pump 5, and/or the first valve 9, and/or the second valve 10, and/or to read out the first sensor unit 15, and/or the second sensor unit 16. The control unit 14 thus enables effective control of the system, a distinction preferably being made between three operating modes.

In the first operating mode, the blood is pumped from the blood circulatory system of the person 1 into the gas exchange chamber 6. This may be achieved, for example, by completely or partially closing the first valve 9, completely or partially opening the second valve 10, and activating the pump 5 so as to pump the blood into the gas exchange chamber 6.

In the second operating mode, the blood in the gas exchange chamber 6 is brought in contact with oxygen under increased pressure. For this purpose, for example, the pump 5 is deactivated, so that a flow between the first tube section 3 and the second tube section 4 is prevented, and moreover the degrees of opening of the first valve 9 and of the second valve 10 are varied, wherein the opening and closing can take place suddenly or in a time-controlled manner. In the second operating mode, oxygen is introduced from the oxygen source 13 by the oxygen supply system 11, via the oxygen supply line 12, into the gas exchange chamber 6, and moreover the gas mixture of supplied oxygen and of carbon monoxide eliminated from the blood is removed via the carbon monoxide discharge line 17. Consequently, a high oxygen concentration is present in the gas exchange chamber 6, while carbon monoxide is removed from the gas exchange chamber 6 via the carbon monoxide discharge line 17, whereby effective elimination of carbon monoxide is implemented.

In the third operating mode, the blood is pumped from the gas exchange chamber 6 back into the blood circulatory system of the person 1. For this purpose, for example, the first valve 9 is closed completely or partially, the second valve 10 is opened completely or partially, wherein the closing and opening can take place suddenly or in a time-controlled manner, and the pump 5 is activated in such a way that the blood is pumped from the gas exchange chamber 6 into the blood circulatory system of the person 1. In this way, it is ensured that blood enriched with oxygen is returned to the blood circulatory system of the person 1.

Repeated execution of the first operating mode, the second operating mode, and the third operating mode results in treatment of the blood in portions and, in this way, makes it possible to eliminate carbon monoxide in a minimally invasive manner using one access, to the blood circulatory system of the person 1, or one cannula 2.

In one embodiment of the invention which is not explicitly shown, the system is designed so as to be accommodated in a portable case and be transportable in a mobile manner. In this way, it is possible to use the system according to the invention locally in ambulances or rescue vehicles or hospitals and doctors' offices.

Figure 2:
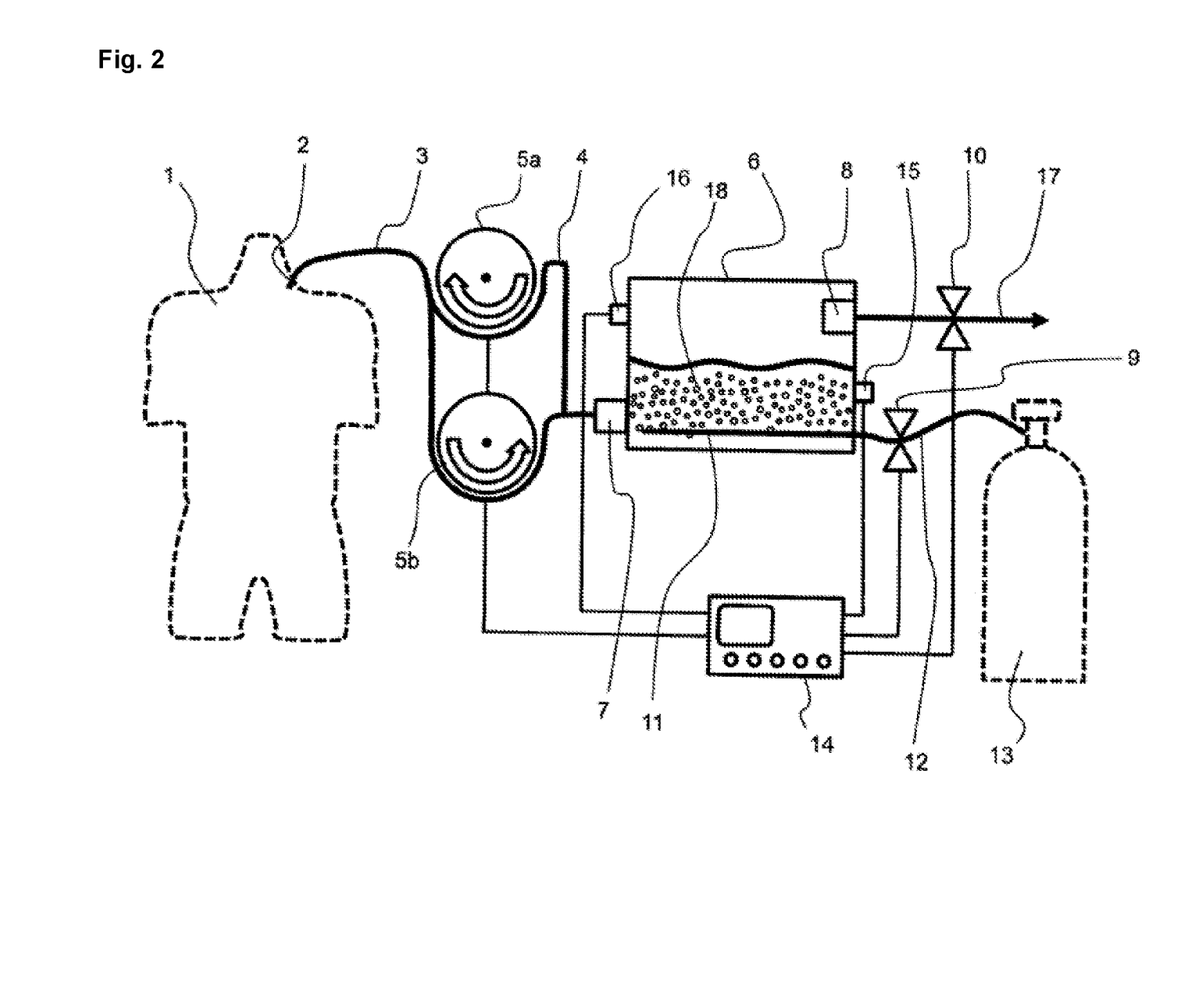
FIG. 2 shows a schematic illustration of the system according to the invention comprising two unidirectional pumps.

FIG. 2 shows a schematic illustration of the invention comprising two unidirectionally operating pumps 5a and 5b. Such a design of the invention offers the option of also using unidirectional pumps 5a and 5b for implementing the system according to the invention. The arrows indicate the direction of flow when the pumps 5a and 5b are activated. Unidirectional pumps 5a and 5b have the advantage that these are less expensive to procure and have a longer service life. In the variant embodiment shown in FIG. 2, the control unit 14 is configured to control the pumps 5a and 5b, and/or the first valve 9, and/or the second valve 10, and/or to read out the first sensor unit 15, and/or the second sensor unit 16. In the first operating mode, for example, the first pump 5a is deactivated, the second pump 5b is activated, the first valve 9 is closed completely or partially, and the second valve 10 is opened completely or partially. In this way, it is ensured that the blood is pumped from the blood circulatory system of the person 1 into the gas exchange chamber 6. In the second operating mode, both pumps 5a and 5b are deactivated, and the degrees of opening of the first valve 9 and of the second valve 10 are varied. In this way, oxygen is pumped into the gas exchange chamber 6, so that carbon monoxide is eliminated at an elevated pressure. In the third operating mode, the first pump 5a is activated, the second pump 5b is deactivated, the first valve 9 is closed completely or partially, and the second valve 10 is opened completely or partially. In this way, in the third operating mode, it is achieved that the blood is pumped back into the blood circulatory system of the person 1. The pumps 5a and 5b shown in FIG. 2 are preferably pumps that, when deactivated, prevent flow between the first tube section 3 and the second tube section 4.

Having a compact design, the system according to the invention for the extracorporeal elimination of carbon monoxide makes it possible to effectively treat blood in portions in a simple manner and, as a result, to immediately implement a fast and minimally invasive therapy of carbon monoxide poisoning at the site of an accident. and/or when transporting the patient.

The invention claimed is:

1. A system for the extracorporeal elimination of carbon monoxide, comprising at least one pump and a gas exchange chamber, the at least one pump being connectable to the blood circulatory system of a person by way of a first tube section connectable to a cannula and being connected to a gas exchange chamber via a second tube section, wherein
the system is configured to transfer blood, via the first tube section, from the blood circulatory system of the person, by way of the at least one pump, into the gas exchange chamber, and to return the blood from the gas exchange chamber to the blood circulatory system of the person, via the same first tube section, the gas exchange chamber has an oxygen supply which is connected to an oxygen source via an oxygen supply line and the oxygen supply line has an outflow element which is configured to form gas bubbles, a flow between the first tube section and the second tube section is prevented by the at least one pump in a deactivated non-pumping state, or the first tube section or the second tube section has at least one valve configured to prevent a flow between the blood circulatory system of the person and the gas exchange chamber, whereby the gas exchange chamber can be operated with the pump deactivated or with the valve preventing the flow and can be pressurized to a pressure above the ambient atmospheric pressure without affecting the person's blood circulatory system.

2. The system according to claim 1, wherein the at least one pump is a single pump which is bidirectionally operable or the at least one pump is two unidirectionally operable pumps with which blood in the first tube section is conveyable in opposite directions and the first tub section is connectable to the two unidirectionally operable pumps.

3. The system according to claim 1, wherein the system further comprises a bubble filter arranged between the second tube section and the gas exchange chamber.

4. The system according to claim 1, wherein each of the at least one pump is a peristaltic pump.

5. The system according to claim 1, further comprising a bubble filter disposed between the second tube section and the gas exchange chamber.

6. The system according to claim 5, wherein the bubble filter comprises pores having a diameter in the range of 5 μm to 80 μm.

7. The system according to claim 1, wherein the oxygen source is an oxygen cylinder.

8. The system according to claim 1, wherein the outflow element comprises a perforated line, a perforated membrane or a porous foam.

9. The system according to claim 1, wherein the gas exchange chamber communicates with a carbon monoxide discharge line.

10. The system according to claim 9, further comprising a foam filter disposed between the gas exchange chamber and the carbon monoxide discharge line.

11. The system according to claim 9, wherein the oxygen supply line comprises a first valve, and the carbon monoxide discharge line comprises a second valve.

12. The system according to claim 11, wherein the gas exchange chamber communicates with a first sensor unit configured to determine a carbon monoxide concentration.

13. The system according to claim 12, wherein the gas exchange chamber communicates with a second sensor unit configured to measure a pressure inside the gas exchange chamber.

14. The system according to claim 13, further comprising a control unit configured to read the first sensor unit and/or the second sensor unit and/or to control the at least one pump and/or the first valve and/or the second valve.

15. The system according to claim 13, wherein the system is configured to treat blood in portions, and wherein the system is configured, in a first operating mode, to pump a portion of the blood from the blood circulatory system of the person into the gas exchange chamber; in a second operating mode, to bring blood in the gas exchange chamber in contact with oxygen under increased pressure and to eliminate carbon monoxide; and, in a third operating mode, to pump blood from the gas exchange chamber back into the blood circulatory system of the person; and the system further comprises a control unit configured to control the first valve and/or the second valve and/or the at least one pump and/or to read the first sensor unit and/or the second sensor unit.

16. The system according to claim 12, further comprising a control unit configured to control the first valve and/or the second valve and/or the at least one pump and/or to read out the first sensor unit.

17. The system according to claim 12, wherein the system is configured to treat blood in portions, and wherein the system is configured, in a first operating mode, to pump a portion of the blood from the blood circulatory system of the person into the gas exchange chamber; in a second operating mode, to bring blood in the gas exchange chamber in contact with oxygen under increased pressure and to eliminate carbon monoxide; and, in a third operating mode, to pump blood from the gas exchange chamber back into the blood circulatory system of the person; and the system further comprises a control unit configured to control the first valve and/or the second valve and/or the at least one pump and/or to read the first sensor unit.

18. The system according to claim 11, further comprising a control unit configured to control the at least one pump and/or the first valve and/or the second valve.

19. The system according to claim 11, wherein the system is configured to treat blood in portions, and wherein the system is configured, in a first operating mode, to pump a portion of the blood from the blood circulatory system of the person into the gas exchange chamber; in a second operating mode, to bring blood in the gas exchange chamber in contact with oxygen under increased pressure and to eliminate carbon monoxide; and, in a third operating mode, to pump blood from the gas exchange chamber back into the blood circulatory system of the person; and the system further comprises a control unit configured to control the first valve and/or the second valve and/or the at least one pump.

20. The system according to claim 1, wherein the system is configured to treat blood in portions, and wherein the system is configured, in a first operating mode, to pump a portion of the blood from the blood circulatory system of the person into the gas exchange chamber; in a second operating mode, to bring blood in the gas exchange chamber in contact with oxygen under increased pressure and to eliminate carbon monoxide; and, in a third operating mode, to pump blood from the gas exchange chamber back into the blood circulatory system of the person.

21. The system according to claim 20, further comprising a control unit configured to control the at least one pump.

22. The system according to claim 1, further comprising a control unit configured to control the at least one pump.

23. A portable case in combination with the system of claim 1, wherein the system is disposed in the portable case and transportable therewith.

24. The combination according to claim 23, wherein the combination is configured to be transportable by a person, even when the system is in use on a person.

25. A system for the extracorporeal elimination of carbon monoxide, comprising at least one pump and a gas exchange chamber which has an oxygen supply which is connected to an oxygen source via an oxygen supply line, wherein the at least one pump can be connected to the blood circulatory system of a person via a first tube section which can be connected to a cannula and is connected to the gas exchange chamber via a second tube section, wherein the system is arranged to perform a stepwise elimination of carbon monoxide via only one access to the blood circulatory system of the person by treating the blood portion by portion by repeatedly performing three operating modes, wherein the system is arranged to convey blood from the blood circulatory system of the person into the gas exchange chamber in a first operating mode and to convey blood from the gas exchange chamber back into the blood circulatory system of the person in a third operating mode, and wherein:

a. the oxygen supply line comprises a first valve and a carbon monoxide discharge line of the gas exchange chamber comprises a second valve, each of which is controllable and by which the pressure within the gas exchange chamber and the flow of oxygen in the form of gas bubbles through the blood is controllable, and b. the system is configured, in a second operating mode, to contact blood in the gas exchange chamber with oxygen at a pressure elevated above atmospheric pressure, and c. in the second operating mode, a flow between the blood circulatory system of the person and the gas exchange chamber is preventable by a third valve in the first or second tube section or the at least one pump deactivated.

* * * * *